United States Patent [19]

Schroepfer, Jr. et al.

[11] Patent Number: 4,897,475

[45] Date of Patent: Jan. 30, 1990

[54] PROCESS FOR SYNTHESIS OF 5α-CHOLEST-8(14)-EN-3β-OL-15-ONE AND OTHER 15-OXYGENATED STEROLS

[75] Inventors: George J. Schroepfer, Jr., Houston; William K. Wilson, Bellaire; Ker-Shi Wang, Galveston; Alemka Kisic, Houston, all of Tex.

[73] Assignee: William Marsh Rice University, Houston, Tex.

[21] Appl. No.: 152,476

[22] Filed: Feb. 5, 1988

[51] Int. Cl.$^4$ .......................... C07J 71/00; C07J 1/00
[52] U.S. Cl. .................................. 540/83; 260/397.5; 260/397.4
[58] Field of Search ............. 260/397.4, 397.47, 397.5; 540/15, 83

[56] References Cited

U.S. PATENT DOCUMENTS 4,202,891 5/1980 Schroepfer, Jr. et al. ....... 260/397.2

OTHER PUBLICATIONS

Wilson et al., Department of Biochemistry and Chemistry, Rice University, 1988, pp. 1-37.
W. K. Wilson et al., J. Org. Chem., 53, pp. 1713-1719, (1988).
A. Windaus et al., Justus Liebigs Ann. Chem., 488, pp. 91-110, (1931).
F. Schenck et al., Chemische Berichte, 69, pp. 2696-2704, (1936).
A. Windaus et al., Justus Liebigs Ann. Chem., 536, pp. 204-216, (1938).
D. H. R. Barton, J. Chem. Soc., pp. 512-522, (1946).
D. H. R. Barton, J. Chem. Soc., pp. 1116-1123, (1946).
D. H. R. Barton et al., J. Chem. Soc., pp. 257-277, (1951).
D. H. R. Barton et al., J. Chem. Soc., pp. 52-63, (1954).
R. B. Woodward et al., J. Chem. Soc., pp. 1131-1144, (1957).
J. C. Knight et al., J. Biol. Chem., 241, pp. 1502-1508, (1966).
E. J. Parish et al., Chem. Phys. Lipids, 18, pp. 233-239, (1977).

G. J. Schroepfer, Jr. et al., J. Biol. Chem., 252, pp. 8975-8980, (1977).
B. N. Conner et al., Chem. Phys. Lipids, 18, pp. 240-257, (1977).
J. Andrieux et al., J. Chem. Soc., Perkin Trans., 1, p. 363, (1977).
M. Anastasia et al., J. Chem. Soc., Perkin Trans., 1, pp. 1821-1824, (1979).
R. J. Chorvat et al., J. Org. Chem., 44, pp. 3974-3976, (1979).
R. E. Dolle et al., J. Org. Chem., 51, pp. 4047-4053, (1986).
R. E. Dolle et al., J. Org. Chem., 53, pp. 1563-1566, (1988).

(List continued on next page.)

*Primary Examiner*—Douglas W. Robinson
*Assistant Examiner*—Joseph A. Lipovsky
*Attorney, Agent, or Firm*—Finnegan, Henderson, Farabow, Garrett & Dunner

[57] ABSTRACT

A process for preparing 15-oxygenated sterols, such as 3β-hydroxy-5α-cholest-8(14)-ene-15 one, comprising converting 7-dehydrocholesterol to 3β-benzoyloxy-cholesta-5,7-diene, converting the 3β-benzoyloxy-cholesta-5,7-diene to a 3β-benzoyloxy-5-cholesta-7,14-diene, converting the 3β-benzoyloxy-5-cholesta-7,14-diene to a 3β-benzoyloxy-14α, 15α-epoxy-5-cholest-7-ene and converting the 3β-benzoyloxy-14α, 15α-epoxy-5-cholest-7-ene to a 15-oxygenated sterol. Preferably, the 3β-benzoyloxy-cholesta-5,7-diene is converted to a 3β-benzoyloxy-5-cholesta-7,14-diene by (i) contacting 3β-benzoyloxy-cholesta-5,7-diene, in a solvent at a temperature of at most about −55° C., with HCl at a concentration of at least about 2.0 M for a time sufficient to convert the 3β-benzoyloxycholesta-5,7-diene to a 3β-benzoyloxy-5-cholesta-7,14-diene; (ii) neutralizing the resultant reaction mixture with a base to prevent formation of a significant amount of 3β-benzoyloxy-5-cholesta-8,14-diene; and (iii) recovering the 3β-benzoyloxy-5-cholesta-7,14-diene.

49 Claims, 3 Drawing Sheets

OTHER PUBLICATIONS

Swern, Organic Peroxides, vol. II, 1971, Wiley-Interscience, New York, pp. 426–427.

Anastasia et al., J. Org. Chem., vol. 46, No. 16, 1981, pp. 3265–3267.

Willstatter et al., Justus Liebigs Ann. Chem., 358, 1908, pp. 267–287.

Bayer, Z., Physiolo. Chem., 3, 1879, pp. 294–311.

Fieser et al., Steroids, Rheinhold Publishing Corp., New York, 1959, pp. 115–119.

Kirk et al., Steroid Reaction Mechanisms, Elsevier Publishing Co., New York, 1968, pp. 292–293.

PROCESS FOR SYNTHESIS OF 5α-CHOLEST-8(14)-EN-3β-OL-15-ONE AND OTHER 15-OXYGENATED STEROLS

FIELD OF THE INVENTION

The present invention relates to improved methods of making certain 15-oxygenated sterol compounds and to intermediates and byproducts formed in manufacturing the sterol compounds. The 15-oxygenated sterol compounds are useful for inhibiting the biosynthesis of mevalonic acid, including all effects derived from inhibition of biosynthesis of mevalonic acid. Effects derived from inhibition of the biosynthesis of mevalonic acid include supression of the biosynthesis of sterols with a resultant reduction in serum cholesterol levels, in animals, and the inhibition of microorganism and cell growth. The 15-oxygenated sterols are also effective to suppress appetite, which effect is believed to be related to their inhibitory activity on the biosynthesis of mevalonic acid and products derived therefrom, most especially cholesterol.

BACKGROUND OF THE INVENTION

In many instances, the suppression of biosynthesis of sterols is desirable. For example, it is often desirable to suppress the formation of the sterol cholesterol in animals, including humans, whereby the serum cholesterol level in the animal will be lowered.

The concentration of cholesterol in blood serum has been correlated with a number of diseases, particularly atherosclerosis. Atherosclerosis is a condition marked by the formation of plaques in the arterial system. Cholesterol and cholesterol esters are major components of these plaques. While the etiology of the disease is not completely known, it appears that an elevated serum cholesterol level contributes to the development and the progression of atherosclerosis.

Cholesterol in animals is derived from two sources, first the intake and absorption of dietary cholesterol and second the biosynthesis of cholesterol from acetate by cells of various organs of the body, e.g., liver, intestines, and skin. The biosynthesis of cholesterol and other sterols from acetate in the body involves a complex sequence of reactions, one of which is the conversion of 3-hydroxy-3-methylglutaryl Coenzyme A into mevalonic acid. This reaction is considered to be a major regulation point in the normal biosynthesis of cholesterol in cells. If the biosynthesis of mevalonic acid can be inhibited in vivo, production of sterols is reduced, and serum cholesterol levels can thereby be lowered.

In British Pat. No. 860,303 certain aryloxy carboxylic acid esters, such as the methyl ester of 2-(4'-chlorophenoxy)isobutyric acid, are proposed for use in suppressing blood cholesterol levels. While this compound has acquired significant importance in the clinical treatment of humans, for various reasons it is not as effective as is desired. Accordingly, more effective compounds for suppressing serum cholesterol levels are of great interest and importance.

Obesity is also a serious health problem. The correlation between excess weight and a number of diseases, particularly cardiovascular diseases, is well-known. Many people, often for psychological or other reasons, find it difficult or impossible to adhere to weight control or weight loss diets. For this reason, techniques for safely and effectively suppressing appetite are greatly needed.

It is known from U.S. Pat. No. 4,202,891, which patent is fully incorporated herein, that certain 15-oxygenated sterols are effective in the inhibition of the biosynthesis of mevalonic acid and of sterols. A number of desirable effects can be derived from the inhibition of the biosynthesis of mevalonic acid, including suppressing the formation of cholesterol in animals, whereby serum cholesterol levels may be lowered.

In addition, the growth and proliferation of the cells of higher organisms and certain microorganisms, such as yeast and fungi, involve the formation of sterols. Accordingly, inhibition of the biosynthesis of mevalonic acid, and thus reducing sterol formation, is effective to inhibit the growth of cells, both normal and tumorous. Furthermore, inhibition of the biological synthesis of sterols has the effect of inhibiting the growth of certain microorganisms, thereby combatting fungal and yeast infections.

In addition to its role in sterol biosynthesis, mevalonic acid is an important percursor of a number of other important constituents of cells. Thus, while bacteria are generally considered to not contain or need sterols, their growth and proliferation requires synthesis of mevalonic acid and the products derived therefrom. Accordingly, inhibition of mevalonic acid biosynthesis should inhibit bacterial growth.

Also the 15-oxygenated sterols and their derivatives are effective to suppress appetite. While the mechanism by which the 15-oxygenated sterols function to suppress appetite is not known, it is believed that this effect is in some way related to the mevalonic acid or sterol biosynthesis inhibiting activity of the 15-oxygenated sterols.

The 15-oxygenated sterols of U.S. Pat. No. 4,202,891 represent desirable compounds that exhibit a high degree of activity. However, the heretofore known processes for manufacturing the 15-oxygenated sterols have proven costly and time consuming. Often very small yields of the desired products have been obtained or the processes proved difficult to carry out on a large scale for various reasons such as requirements for extensive chromatography. In addition, known processes for the production of 3β-benzoyloxy-5-cholesta-7,14-diene, a key intermediate in the production of 15-oxygenated sterols from 7-dehydrocholesterol, have been unsatisfactory because known procedures are highly variable. On occasion the desired product was obtained in reasonable yield with a reasonable degree of purity; however, frequently the yield and purity were much lower than desired and unknown side products were observed.

The present invention provides a procedure for production, on a large scale, of high quality 15-oxygenated sterols in consistent high yields. Such a procedure, of course, provides corresponding effectiveness and efficiency.

SUMMARY OF THE INVENTION

In accordance with the present invention, a new four step process is provided for the synthesis of 15-oxygenated sterols from dehydrocholesterol. The process includes conversion of 7-dehydrocholesterol to a 3β-benzoyloxycholesta-5,7-diene (step 1), conversion of the 3β-benzoyloxycholesta-5,7-diene to a 3β-benzoyloxy-5(α or β)-cholesta-7,14-diene (step 2), conversion of the 3β-benzoyloxy-5(α or β)-cholesta-7,14-diene to a 3β-benzoyloxy-14α, 15α-epoxy-5(α or β)-cholest-7-ene (step 3), and, finally, conversion of the 3β-benzoyloxy-14α, 15α-epoxy-5 (α or β) cholest-7-ene to a 15-oxygenated sterol, (step 4).

More specifically, the present invention provides a highly desirable technique for converting 3β-benzoyloxy-cholesta-5,7-diene to 3β-benzoyloxy-5(α or β)-cholesta-7,14-diene (step 2) by a process comprising: (i) forming a first reaction mixture by contacting 3β-benzoyloxycholesta-5,7a-diene, in a solvent at a temperature of at most about −55° C., with HCl at a concentration in said solvent of at least about 2.0M for a time sufficient to convert the 3β-benzoyloxycholesta-5,7-diene to 3β-benzoyloxy-5-cholesta-7,14-diene; (ii) neutralizing the reaction mixture with a base to prevent formation of a significant amount of 3β-benzoyloxy-5-cholesta-8,14-diene; and (iii) recovering the 3β-benzoyloxy-5-cholesta-7,14-diene.

DESCRIPTION OF PREFERRED EMBODIMENTS OF THE INVENTION

Figure 1:
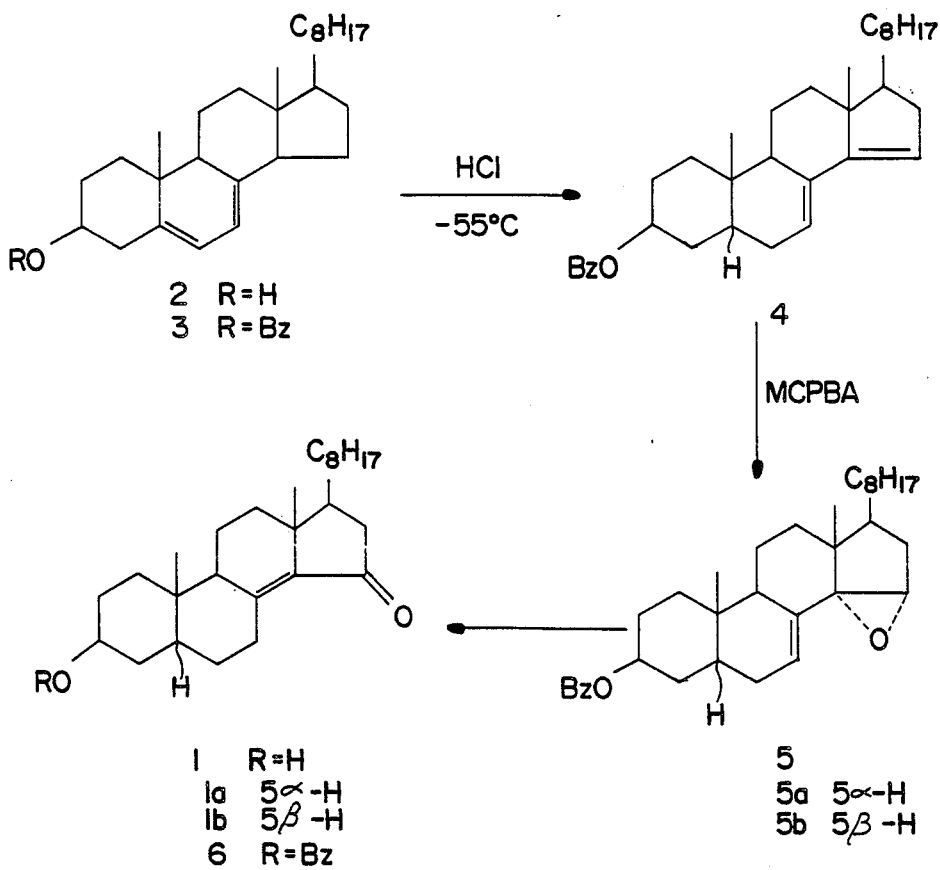
FIG. 1 represents a schematic flow chart of a reaction sequence according to the present invention along with corresponding structural formulae.
Figure 3:
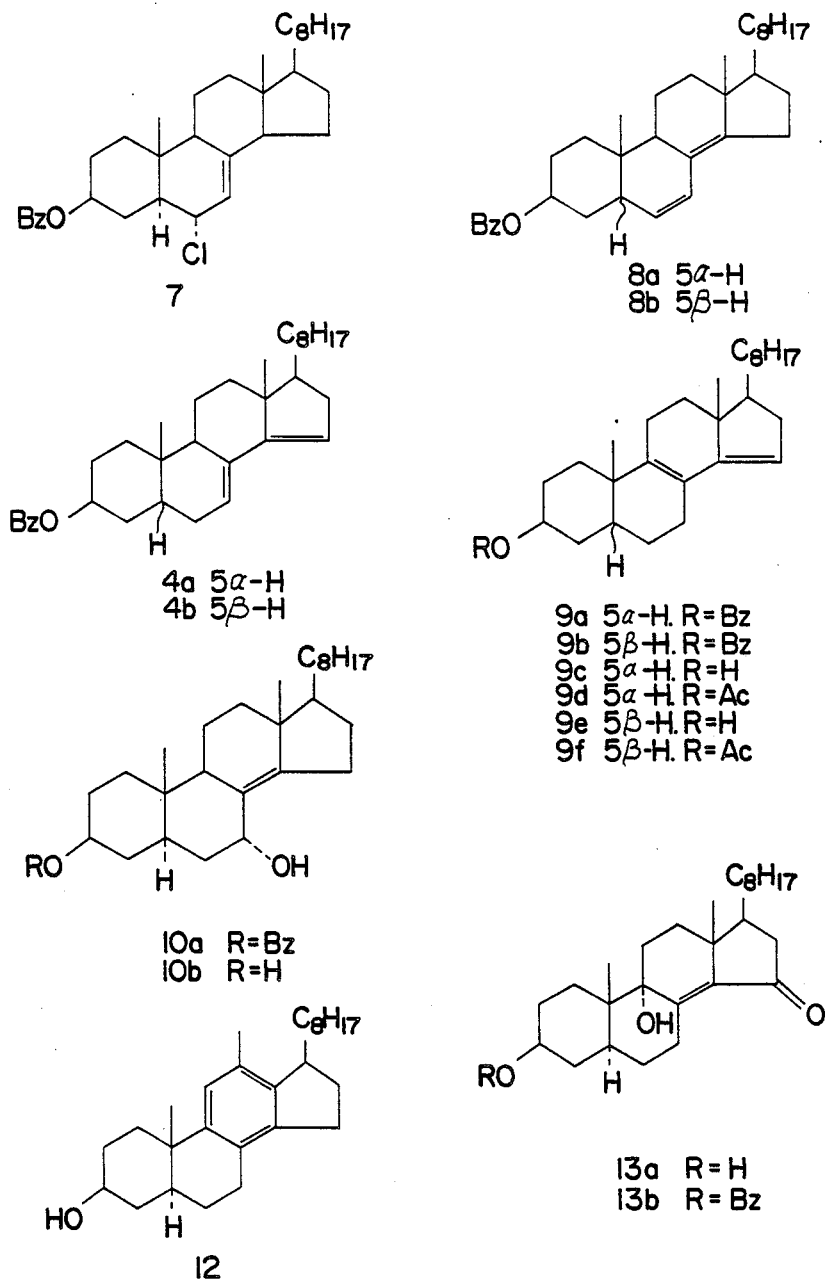
FIG. 3 represents detailed structural formulae of certain compounds discussed in the present specification.

The compounds discussed herein are each assigned a reference number, which reference numbers are correlated in FIGS. 1 and 3 to the corresponding structural formulae.

The present invention relates to an improved synthesis technique for preparing such 15-oxygenated sterols as 3β-hydroxy-5α-cholest-8(14)-en-15-one (1a) from 7-dehydrocholesterol (2). Such a process is generally disclosed in Parish et al., Chemistry and Physics of Lipids, 18, 233–239, 1977; Schroepfer et al., Journal of Biological Chemistry, 252, 8975–8980, 1977. However, the present improved process is more suitable for use on a large-scale and is more capable of consistently producing a high yield of a relatively pure product. Development of the process of the present invention has involved, inter alia, the isolation and identification of intermediates and side products produced in the various process steps as well as appreciation of their implications.

The present invention, as a broadly embodied, involves conversion of 7-dehydrocholesterol (2) to 3β-benzoyloxycholesta-5,7-diene (3), conversion of 3β-benzoyloxycholesta-5,7-diene to 3β-benzoyloxy-5-cholesta-7,14-diene (4), conversion of the 3β-benzoyloxy-5-cholesta-7,14-diene to a 3β-benzoyloxy-14α, 15α-epoxy-5-cholest-7-ene (5), and, finally, conversion of said 3β-benzoyloxy-14α, 15α-epoxy-5-cholest-7-ene to a 15-oxygenated sterol, preferably, 3β-hydroxy-5α-cholest-8(14)-en-15-one (1a).

In accordance with a preferred embodiment of the present invention, 3β-benzoyloxy-cholesta-5,7-diene is converted to a 3β-benzoyloxy-5-cholesta-7,14-diene by a process comprising: (i) contacting 3β-benzoyloxycholesta-5,7-diene, in a solvent at a temperature of at most about −55° C., with HCl at a concentration of at least about 2.0M for a time sufficient to convert the 3β-benzoyloxycholesta-5,7-diene to said 3β-benzoyloxy-5-cholesta-7,14-diene; (ii) neutralizing the resultant reaction mixture with a base to prevent formation of a significant amount of 3β-benzoyloxy-5-cholesta-8,14-diene (8a and 8b); and (iii) recovering the 3β-benzoyloxy-5-cholesta-7,14-diene.

Preparation of Benzoate (Step 1). Conversion of 7-dehydrocholesterol (2) to the $\Delta^{5,7}$ benzoate (3) can be accomplished by known techniques, such as reacting (2) with benzoyl chloride. The reactants may be refluxed in a solvent, such as pyridine and the product recovered by filtration after cooling the reaction mixture. A high purity product can be obtained in a high yield by washing (e.g., with water and dilute carbonate) and recrystallization (e.g., in hot $CHCl_3$).

Diene Isomerization (Step 2). Prior techniques for conversion of the $\Delta^{5,7}$ diene (3) to the 5α-$\Delta^{7,14}$ isomer (4a) have proven to produce highly variable results. Yields varied from 30% (or less) to 70%. Furthermore, despite attempts to maintain constant reaction conditions, the desired product 4a was often contaminated with variable amounts of several different compounds. Even more complexity with respect to product composition was observed in attempts to obtain a second crop of the product from the initial crystallization. Moderate variation of such factors as reaction temperature, purity of the starting material and solvents, duration of reaction, and temperature of quenching of the reaction had little or no discernable effect on product composition.

Isolation and identification of the major intermediates and side products in the reaction were undertaken in an attempt to develop optimum reaction conditions. In preparing the 5α-$\Delta^{7,14}$ isomer by contacting the $\Delta^{5,7}$ diene with HCl at a low temperature, the principal intermediate was found to be 3β-benzoyloxy-6α-chloro-5α-cholest-7-ene (7), along with minor amounts of species 8a and 9a. The principal side product was found to be the 5β-$\Delta^{8,14}$ isomer 9b. The 3β-benzoyloxy-5β-cholesta-7,14-diene isomer 4b was also isolated as a minor side product. The structures were determined by conventional analytical techniques, such as NMR and x-ray crystallography, familiar to those having skill in the art.

Although chloro intermediates in the diene isomerization of sterols were proposed by D. H. R. Barton, Journal Chemical Society, 512–522 (1946), over forty years ago, such an intermediate has not previously been isolated or identified. Additionally, while 5β-isomers have been previously reported in sterol diene isomerizations, see, for example, D. H. R. Barton, Journal Chemical Society, 1116–1123 (1946), the formation of 5β-dienes by low-temperature addition of HCl to a $\Delta^{5,7}$ system has not previously been reported.

Figure 2:
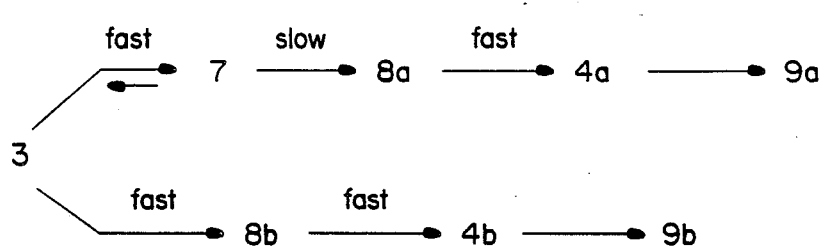
FIG. 2 represents a more detailed schematic flow chart of the reaction sequence, showing intermediates and by products produced by the process of the present invention.

A proposed pathway for the diene isomerization depicted in FIG. 1 (3→4) is shown in FIG. 2 with the principal intermediates and side products indicated. Isomerization of the 5β-dienes appears to follow a pathway similar to that for the 5β-dienes. However, as discussed below, the reaction rates appear to be different for the 5α and 5β systems, and no chloro intermediate corresponding to 7 has been observed in the 5β-sterol pathway. Analysis of the total reaction product indicated that approximately 20% of the initial protonation of the $\Delta^{5,7}$ systems occurred so as to give 5β-sterols. Since the 5β-dienes constitute the bulk of the impurities in the isomerization reaction, any attempts to further increase the yield of the desired product 4a would require modifications of conditions to further favor the initial addition of HCl to the α face of the sterol.

For purposes of producing 5α sterols, it is advantageous to reduce the principal side product 4b. However, 15-oxygenated 5β-sterols are also potent inhibitors of sterol biosynthesis. Thus, production of both the key intermediate 4a and the side product 4b is advantageous. Accordingly, both are within the scope and spirit of the present invention.

Further, it should be apparent that although the discussion focuses on the production of 5α-sterols, processes for producing 5β-sterols from the side product 4b are the same as those for producing 5α-sterols from 4a. Accordingly, the process disclosed herein with regard to 5α-sterols applied equally as well to 5β-sterols and the use of either the 4a or 4b intermediate is within the scope and spirit of the invention.

Once the various species in the diene isomerization have been identified and characterized by conventional techniques, such as $^1$H and $^{13}$C NMR, TLC and HPLC, the course of the reaction can be followed by periodically analyzing aliquots of the reaction. The results of this analysis indicate that the $\Delta^{5,7}$ isomer reacts very rapidly to form 7. This 1,2 addition of HCl to the $\Delta^{5,7}$ system contrasts with the 1,4 addition proposed by Barton, *J. Chem. Soc.* 1946, 512–522, and with the preferred Markovnikov addition of HCl to $\Delta^5$ steroids. See, e.g., Barton, Experientia, Suppl. II, 1955, 121–136. The slow step of the reaction appears to be the dehydrohalogenation of 7, which bears a pseudoequatorial chlorine. It has been found that, at low temperatures, this elimination requires a rather high concentration of HCl, suggesting the intermediacy of the pseudo-axial 6β-epimer of 7. Consistently low levels of the 5α-$\Delta^{6,8(14)}$ isomer 8a were observed as the reaction progressed, suggesting that conversion of 8a to the 5α-$\Delta^{7,14}$ diene 4a is much faster than the dehydrohalogenation of 7. The isomerization of 4a to the 5α-$\Delta^{8,14}$ isomer 9a appears to be somewhat slower than the dehydrohalogenation of 7, since it was discovered that the reaction can be quenched at an optimal time when 7 has completely reacted yet only minor amounts of the 9a isomer have formed.

Based on these observations, a procedure was developed for consistently obtaining good yields and high product purity in the isomerization reaction, i.e., the process for preparing 4a. Generally, the reaction was carried out at a low temperature (no more than about −55° C. and preferrably between −65° and −75° C.). Low temperature promotes the solubility of HCl in the solvent and retards formation of the 5α-$\Delta^{8,14}$ isomer 9a, thereby insuring that the time period for optimal quenching of the reaction is not too short. By adding CH$_2$Cl$_2$ to a CHCl$_3$ solvent, it is possible to lower the freezing point without adversely affecting solubility of the $\Delta^{5,7}$ isomer 3. A solvent mixture of CHCl$_3$ and CH$_2$Cl$_2$ in a weight ratio of about 3:1 has proven to be satisfactory. Of course, other solvents or solvent mixtures that have a low freezing point and good solubility for HCl and the $\Delta^{5,7}$ isomer may be used.

To counteract the tendency of the starting material to crystallize out at low temperature, HCl gas is preferably introduced rapidly until a concentration of about 2.0 −2.5M is obtained. After the flow of HCl is shut off, the conversion of 7 to 4a is allowed to proceed at no more than −55° C., and preferably between −65° to −70° C. The reaction can be monitored periodically, such as by chromatography (e.g., TLC) on a aliquot of the reaction mixture, to determine the optimal quenching time.

After the $\Delta^{5,7}$ diene (3) has been isomerized to the $\Delta^{7,14}$ intermediate (4a), but prior to the production of any significant amount of $\Delta^{8,14}$ byproduct (9a), the reaction solution is quenched (neutralized) with a base such as NH$_4$OH. Subsequent to quenching and extraction of the product, an additional base such as pyridine may be added to the CHCl$_3$ solution to neutralize any additional HCl released from the dehydrohalogenation of 7, thus preventing HCl-catalyzed isomerization of the 5α-$\Delta^{7,14}$ isomer 4a to the 5α-$\Delta^{8,14}$ isomer 9a.

Partial evaporation of the CHCl$_3$ extracts followed by addition of a polar solvent such as acetone produces a precipitate composed of about 90% 4a and about 10% 9a and 9b (combined). Using this procedure, twelve consecutive reactions (700–1000 g scale) gave 77–84% (average 82%) yields of 4a of 83–91% purity (average 88%).

The 5β-isomers produced along with the 5α-isomers can be easily separated from the 5α-isomers by recrystallization from CHCl$_3$-acetone (1:2), but the 5α-isomers, especially the 5α-$\Delta^{7,14}$ and 5α-$\Delta^{8,14}$ isomers 4a and 9a, are not, on a preparative scale, readily separated by recrystallization or chromatography. $^{13}$C NMR provides the most useful approach for compositional analysis of reaction mixtures derived from the treatment of the $\Delta^{5,7}$ diene 3 with HCl since all of the known components can be resolved without decomposition. Most of the diene species could be resolved by $^1$H NMR, capillary GC, and reversed-phase HPLC; however, the chloro intermediate 7 was unstable upon chromatography. Compositional analysis of mixtures of any pair of dienes (including 7) could be carried out by $^1$H NMR by examination of either the 3α-H, vinyl, or methyl $^1$H NMR resonances, but in more complex mixtures, overlap of these peaks precluded quantitation. Decomposition of the sterol benzoates was a major inpediment to quantitation by capillary GC. This problem can be overcome by using a very clean column. However, even under these conditions, the 5α-$\Delta^{7,14}$ and 5α-$\Delta^{8,14}$ peaks (for 4a and 9a) are barely resolved. Reversed-phase HPLC gave fairly good resolution of all dienes except for 4a and 9a. Normal-phase HPLC of sterol benzoates is unsatisfactory because of excessive peak tailing.

The isolation of 5β-dienes has not been reported previously in low-temperature isomerizations of $\Delta^{5,7}$ dienes. From the isomerization of a 5β-$\Delta^{6,8(14)}$ acetate, Windaus et al., *Justus Liebigs Ann. Chemistry*, 536, 204–216 (1938) isolated a new diene which was later identified by D. H. R. Barton, *Journal Chemical Society*, 1946, 1116–1123 as the 5β-$\Delta^{8,14}$ diene acetate 9f. Saponification and acetylation of the 5β-$\Delta^{8,14}$ species 9b gave a diene acetate 9f virtually identical in melting point, UV spectrum, and optical rotation with the Windaus diene.

A more recent example of a 5β-diene is the reported isolation in the ergosterol series of a 5β-$\Delta^{6,8(14)}$ diene, which was unexpectedly resistant to acid isomerization to other dienes under refluxing with aqueous HCl/ethanol. See J. Andrieux, D. H. R. Barton, H. Patin, *Journal of the Chemical Society*, Perkin Transactions 1, 359–363 (1977). Surprisingly, no 5β-$\Delta^{8,14}$ species was observed when ergosterol was subjected to the Fieser conditions. See Fieser et al., *Journal American Chemical Society*, 74, 5397–5403 (1952).

Although the major side product of diene 3 isomerizations in CHCl$_3$ is 9b, the major side product of one reaction in CH$_2$Cl$_2$ was the 5$\beta$-$\Delta^{7,14}$ species 4b. Apparently, 4b was converted to the 5$\beta$-$\Delta^{8,14}$ species 9b more slowly in CH$_2$Cl$_2$ than in CHCl$_3$/CH$_2$Cl$_2$ (4:1). Another major side product of this reaction in CH$_2$Cl$_2$ was found to be 3$\beta$-benzoyloxy-5$\alpha$-cholest-8(14)-en-7$\alpha$-ol (10a). The structure of 10a was established by hydrolysis to the known diol 10b. Compound 10a probably arose during workup from a cationic or chloro intermediate formed by protonation or addition of water to either the 5$\alpha$-$\Delta^{6,8(14)}$ or 5$\alpha$-$\Delta^{7,14}$ species (8a or 4a).

No 5$\beta$-epimer of chloro intermediate 7 has been detected. If 1,2 addition of HCl occurs in a syn manner, then the resulting 6$\beta$-chloro substituent would be pseudo-axial and, unlike 7, capable of facile elimination to the 5$\beta$-$\Delta^{6,8(14)}$ species 8b. Diene 8b is believed to be an intermediate, isolated in impure form.

In dilute (1%) solution in ethyl acetate or benzene, 7 was demonstrated to be stable for 12 days. In methanol or ethanol or in concentrated CHCl$_3$ solution, 7 decomposed within 5 hours to a mixture of dienes 3, 8a, and a component which probably represents 3$\beta$-benzoyloxy-5$\alpha$-cholesta-6,8-diene(11). Little dehydrohalogenation was observed after 3 hours for 2% solutions of 7 in CHCl$_3$ or in CHCl$_3$ containing 10% triethylamine or pyridine. Upon slow heating (10 min) in a capillary tube, 7 melted as low as 135° C. At a normal heating rate for melting point determination, 7 melted at 154°–155° C. These combined observations suggest that HCl promotes the decomposition of 7; the HCl released then further accelerates the decomposition. The rapid decomposition of 7 in alcohols may stem from catalytic release of HCl by nucleophilic substitution by the alcohol.

Epoxidation and Hydrolysis to Ketone 1 (Steps 3 and 4). The $\Delta$7,14 diene 4a can be epoxidized to 5a following known modifications shown in Parish et al., Chem. Phys. Lipids 18, 233–239 (1977), i.e., treatment of 4a with m-chloroperbenzoic acid (MCPBA). The known process could not be readily scaled up because of the limited solubility of 4a in ether.

The known epoxidation procedure can be improved by the addition of solid NaHCO$_3$ to the reaction mixture to neutralize 3-chlorobenzoic acid (present both as a contaminant in m-chloroperbenzoic acid and as a product of the epoxidation reaction) and thereby prevent the acid-catalyzed decomposition of the epoxide product. In addition, it has been found desirable to add the MCPBA to the reaction mixture at a higher temperature than shown in Parish, id., in order to prevent precipitation of the starting material.

From 164 epoxidation reactions carried out on a 140 g scale, yields of 57–68% (average 63%) were obtained, or 65–81% (average 72%) assuming 88% purity for the starting diene 4a. The purity of the epoxide 5 was judged by melting point (mp) since techniques such as $^1$H NMR, TLC and HPLC did not reveal any impurities for samples of 5 melting 12° C. lower than the normal mp of 211° C. Lower-melting samples of 5 gave significantly lower yields (50% vs. 65%) in the subsequent conversion to 1.

Epoxide 5 can be hydrolyzed to 6 in just 5 min and, on a 5 g scale, afforded an 82% yield. However, on a 200 g scale, purification of the intermediate 6 consumes vast amounts of time and solvent, and typical yields were only about 50%. Scaling up the existing procedure for converting 6 to 1 is also hampered by the limited solubility of 6 in the hydrolysis solvent: using a 5 liter flask, this reaction could be carried out on only a 30–40 g scale.

In accordance with the known procedure, intermediate 6 is subsequently hydrolyzed to 1. However, the reagent for both steps is mineral acid in an organic solvent (milder conditions being used in the first step), and it has been found that the two steps may be combined. Specifically, it was found that the conditions for transforming 6 to 1 were also sufficient for transforming 5 to 1. In order to carry out 120 g scale reactions in a 5 liter flask, the reaction was allowed to begin with large amounts of undissolved 5, which went into solution as the reaction progressed. In the two-step reaction, the first step produced side products generally less polar than 6, and the second step gave side products generally more polar than 1. In the one-pot reaction, 1 had to be separated from both more and less polar side products. This separation was achieved by using a two-phase recrystallization from hexane/methanol/water: the polar impurities remained in the methanol/water phase, the non-polar impurities remained in the hexane phase, and 1, being soluble in neither phase, crystallized out at the interface in long, large needles.

After two such recrystallizations, samples of 1 contained less than 1% non-polar impurities and approximately 5% polar impurities. Filtration through silica gel using a relatively nonpolar solvent (CH$_2$Cl$_2$ or CHCl$_3$) afforded 1 of greater than 99% purity. Using the procedure of the present invention, 101 hydrolyses of 5 on a 120–140 g scale gave greater than 99% pure 1 in 58–71% yield (average 65%).

The major side products of the one pot conversion of 5 to 1 were the benzoate ester 6 and the aromatic ring C sterol 12. The configuration of 12 at C-17 was established to be 17$\alpha$(H) by comparison of the NMR chemical shifts (17-H and 21-H$_3$) with those reported for 12 and its epimer at C-17. Three minor side products were also isolated: 9$\alpha$-hydroxy derivatives of 1 and 6 (13a and 13b) and a keto-diol.

When 1 or 6 was subjected to the hydrolysis conditions for converting 5 to 1, the recovered 1 was found to contain several impurities. Conducting the reaction under argon reduced the amount of impurities somewhat compared to reactions in air. The absence of 12 in these impurities indicates that neither 1 nor 6 is an intermediate in the formation of 12. The formation of 12 from $\alpha$, $\beta$-unsaturated sterol epoxides has been previously studied and appears to involve a 7,9 (11),14-triene intermediate.

In summary, there has been described significant improvements in the synthesis of ketone 1 from 7-dehydrocholesterol 2 so that the reactions can be carried out on a large scale in a reasonably short period of time. The synthesis has been shortened to four steps, for which the average yields for the individual steps were 97%, 82% (88% purity), 63%, and 65%. The overall average yield for conversion of 7-dehydrocholesterol to 1 was 33%. The highest yields for the individual steps were 97%, 84%, 68%, and 71%, giving an overall best yield of 39%, which is at least 40% higher than previously reported for the syntheses of 1. The present invention also provides for a much-improved large-scale synthesis of epoxide 5, which is a key intermediate not only in the synthesis of 1 but also in the synthesis of a number of other 15-oxygenated sterols.

In the course of optimizing the conditions for each step in this synthetic scheme, major side products of these reactions have been isolated and identified. In addition, new intermediates and side products in the diene isomerization reaction have been discovered, findings which have significant implications with respect to the mechanism and use of this reaction. For example, the reason high HCl concentrations are required for the diene isomerization at low temperature is to promote the dehydrohalogenation of the chloro intermediate 7, the slow step in the overall conversion of 3 to 4a. Furthermore, under conditions developed herein, the $5\alpha$-$\Delta^{7,14}$ diene 4a can be obtained with only minor amounts of the $5\alpha$-$\Delta^{8,14}$ isomer 9a; the 5–15% $\Delta^{8,14}$ contaminant observed is mainly the $5\beta$-$\Delta^{8,14}$ isomer 9b, which can be removed by recrystallization.

With reference to the following Examples, the invention will now be described in further detail. The examples are for illustration purposes and are in no way intended to limit the scope or spirit of the present invention.

EXAMPLE I $3\beta$-Benzoyloxycholesta-5,7-diene (3)

In a 5 liter round bottom flask are placed 1000.0 g (2.60 moles) 7-dehydrocholesterol (Chemical Dynamics, containing 3.3% methanol), 2.4 liters dry pyridine (Aldrich Gold Label, 0.05% water), and 550 mL (4.74 mol) benzoyl chloride (Aldrich, 99%). The contents are swirled briefly, heated rapidly (15 min) to boiling, and refluxed for 5 min. A small (approximately 200 mL) bottom layer of pyridinium chloride (composition by $^1$H and $^{13}$C NMR analysis) normally forms and solidifies when the reaction mixture is cooled. After 30 min of cooling in air, the dark reaction mixture is poured over ice, swirled, and allowed to stand at 20° C. for 1–2 hours. The precipitate which forms is collected by suction filtration. The filter cake is washed successively with 7 liters of water, 4 liters of dilute sodium carbonate, 7 liters of water, and 4 times with 500 mL of acetone. The filter cake is pulverized and allowed to dry in air overnight. The crude product (97–105% yield) shows a single spot by TLC (silica gel eluted with toluene/hexane 1:1, $R_f$ 0.58) and melts at 140°–144° C, clearing at 191° C. It appeared to be pure by $^1$H and $^{13}$C NMR except for a trace (less than 1 mole %) of methyl benzoate. The excess mass (up to 8%) of some samples is apparently water.

Although the crude product gives satisfactory results in the subsequent diene isomerization, this material is normally recrystallized by dissolving it in 2 liters of hot CHCl$_3$ (the small aqueous phase which forms is ignored) and precipitating the sterol by addition of 5 liters of acetone. After cooling and subsequent storage overnight at $-20°$ C., the crystals are filtered, washed twice with 300 mL of cold acetone, and dried to constant mass. The yield of white crystals was 1193 g (97% yield). In one run, no impurities were detected at the 1% level by $^1$H or $^{13}$C NMR, and a single spot was observed on TLC at $R_f$ 0.58 (solvent, toluene/hexane 1:1).

Two recrystallizations of 5.00 g of this material from hot acetone/CHCl$_3$ gave an analytical sample (2.7 g of colorless needles). Values obtained by standard analytical methods conform well to previously reported values.

Four consecutive reactions carried out on a 700 g scale gave similar results with yields of 836, 838, 836, and 827 g (average, 834 g; 97% yield, based on 3.3% methanol in the starting 7-dehydrocholesterol) and virtually identical physical constants.

A sterol material balance carried out for this reaction showed that the acetone washings contained only pyridine and methyl benzoate and that the filtrate from recrystallization contained a mixture of sterols (1.9% of total sterol mass).

EXAMPLE II $3\beta$-Benzoyloxy-$5\alpha$-cholesta-7,14-diene (4a), large-scale preparation A solution of 1000 g of 3 in a mixture of CHCl$_3$ (3000 mL) and CH$_2$Cl$_2$ (800 mL) is prepared in a 5 liter round bottom flask fitted with a thermometer, a gas dispersion tube, an outlet port, and a mechanical stirrer. The flask is rapidly cooled to $-55°$ C., and HCl gas is bubbled through the partially crystallized reaction mixture at a flow rate of 50 on a Gilmont size 2 flowmeter (Gilmont Instruments, Great Neck, NY). The reaction mixture is further cooled as rapidly as possible to $-65°$ to $-70°$ C. over the next 30–40 minutes, and then the HCl flow is increased to 100 on the flowmeter. These flow and temperature conditions are maintained until the HCl concentration is 2.0–2.5M (determined by titration of a reaction aliquot with standard base). The HCl flow is then shut off, and the reaction monitored every 15–30 min by TLC (silica gel spotted with a neutralized, washed aliquot of the reaction mixture and developed with toluene/hexane 1:1). The reaction is considered complete when, instead of 3 overlapping spots at $R_f$ 0.50, 0.55, and 0.60, only a single spot at $R_f$ 0.55 is observed. Most of the HCl is then evaporated in vacuo over the next 40–60 minutes by drawing the HCl vapors through a sodium hydroxide trap using a water aspirator.

The reaction mixture is neutralized by pouring (with vigorous swirling) 600 mL portions of the cold, dark reaction mixture into a 2 liter Erlenmeyer flask containing 500 g of ice and 150 mL of concentrated NH$_4$OH. The neutralized mixtures are combined in a 6 liter separatory funnel, the aqueous phase discarded, the organic phase washed twice with 2.5 liters of water, and the lower phase immediately drained into 120 mL of pyridine. The cloudy organic layer becomes clear after a few minutes, and the solution is drawn into the continuous feed tube of a rotary evaporator, typically leaving behind a small aqueous layer. The (often turbid) solution is concentrated from about 5 liters to 3.0 liters and divided into two portions. Acetone (total 3.0 liters) is then added rapidly with swirling. Crystallization is allowed to proceed for a few minutes, an additional 3.0 liters of acetone is added, and the mixture is stored overnight at 4° C. The crystals are collected by suction filtration, washed twice with 100 mL of acetone, pressed very dry, pulverized, and dried to constant mass.

A white powder (815–841 g) containing $\Delta^{7,14}$ diene 4a in 83–88% purity is obtained. The impurities are a mixture of sterol benzoates (principally 9a and 9b). The former (but not the latter) impurity can be removed by recrystallization from acetone/CHCl$_3$ (2:1) as described above. The yield and purity ranges given above are based on six 1000 g scale reactions. The best reaction gave 836 g (84% crude yield) of material which assayed at 88% purity. (A second crop obtained from concentration of the filtrate consisted of 4a and 9b in a 1:4 ratio.)

This 88% pure product was assayed by $^1$H NMR (comparison of the intensities of the $\Delta^{7,14}$ vinyl peaks at $\alpha 5.76$ and $\alpha 5.52$ with the height of the 5$\alpha$- $\Delta^{8,14}/5\beta$-$\Delta^{8,14}$ peak at $\alpha 5.4$), HPLC (comparing the intensity of the 4a/9a peak with that of the 9b peak), by capillary GC (comparing the intensity of the partially resolved 4a/9a peak with that of the 9b peak), by TLC (single spot at $R_f=0.53$ on silica gel developed with toluene/hexane 1:1 and $R_f 0.35$ on silica gel coated with AgNO$_3$ developed with toluene/hexane 1:1), and by mp (151°–153° C.; 98% pure 4a melts at 154.4°–156° C., vide infra).

EXAMPLE III

3β-Benzoyloxy-5α-cholesta-7,14-diene (4a), analytical sample

A diene isomerization was carried out on a 450 g scale using the procedure described above. The first crop of 269 g (60% yield) of white solid (assayed by $^1$H NMR at 94% 4a, contaminated mainly with 9b) was recrystallized by dissolving it in 700 mL of hot CHCl$_3$ containing 1 mL pyridine and adding 1.0 liter of hot acetone. The product was collected after 24 hr to give 220 g of colorless crystals of 4a of 95% purity ($^1$H NMR). Two additional recrystallizations gave 181 g (98% purity) and 127.8 g (98% purity). The structure and purity were confirmed by standard analytical techniques. Because no impurities could be detected by HPLC analysis, the 2% $\Delta^{8,14}$ impurity observed in the $^1$H NMR spectrum was judged to be 9a.

Concentrations of diene intermediates as the reaction progresses. A diene isomerization was carried out as described above but using 20 g of 4a in 120 mL of CHCl$_3$/CH$_2$Cl$_2$ (4:1). The reaction was cooled to $-55°$ C., a saturated solution of HCl in CHCl$_3$ (30 mL, $-55°$ C.) was added, and HCl was allowed to bubble through the reaction mixture for 20 m in. Then the HCl was shut off, and the reaction was held at $-65°$ C. At various times (2, 6, 17, 26 55, 75, 115, 160, 220, and 300 min) approximately 10 mL aliquots were removed from the reaction and poured into cold concentrated NH$_4$OH. The resulting organic layer was washed with water, rotary evaporated to an oil or solid, and dissolved in CDCl$_3$ (deuterated chloroform, C$^2$HCl$_3$) immediately prior to $^1$H and $^{13}$C NMR analysis. The results of the NMR analysis appear in Table I. An analogous experiment carried out on a 200 g scale gave similar results.

TABLE I

Relative concentration of diene intermediates and products.[a]

| Compound | Time (min) | | | | | | | | | | |
|---|---|---|---|---|---|---|---|---|---|---|---|
| | 0 | 2 | 6 | 17 | 26 | 55 | 75 | 115 | 160 | 220 | 300 |
| | Relative concentrations | | | | | | | | | | |
| 3 | 100 | 0.5 | 0.1 | 0.2 | 0 | 0 | 0 | 0 | 0 | 0 | 0 |
| 7 | 0 | 46 | 49 | 24 | 5 | 0 | 0 | 0 | 0 | 0 | 0 |
| 8a | 0 | 2 | 2 | 2 | 3 | 2 | 3 | 2 | 4 | 2 | 2 |
| 11 | 0 | 1 | 2 | 0.5 | 0 | 0 | 0 | 0 | 0 | 0 | 0 |
| 4a | 0 | 27 | 26 | 54 | 76 | 78 | 70 | 75 | 73 | 76 | 34 |
| 9a | 0 | 0 | 0 | 0 | 0 | 0 | 3 | 2 | 2 | 4 | 19 |
| 8b | 0 | 3 | 0 | 5 | 5 | 0 | 0 | 0 | 0 | 0 | 0 |
| 4b | 0 | 15 | 18 | 8 | 0 | 2 | 0 | 0 | 0 | 0 | 0 |
| 9b | 0 | 0 | 0 | 5 | 9 | 14 | 13 | 15 | 14 | 16 | 16 |
| d | 0 | 4 | 2 | 1 | 0 | — | 6 | 3 | 7 | 2 | 2 |
| e | 0 | 1 | 2 | 2 | 2 | — | 3 | 2 | 2 | 2 | 2 |

[a]Concentrations (±5% absolute for values ≧10%, ±2% absolute for values <10%) determined on quenched reaction aliquots by a combination of $^1$H and $^{13}$C NMR.
[b]Sample partially decomposed during work-up. Measured values for 7, 8a, 4a, 9a, 4b, and 9b were 16, 10, 43, 11, 0, and 13%. Values shown were estimated by postulating that 7, 4a, and 4b were partially converted to 8a, 9a, and 9b during decomposition.
[c]The reaction was allowed to warm to 15 C during the last hour. The product was only partially soluble in CDCl$_3$ and contained several minor impurities; accordingly, the percentage compositions were normalized to give 9b a value of 16%.
[d]Unknown substance having a $^1$H NMR singlet at δ 0.74.
[e]Unknown substance having a $^1$H NMR singlet at δ 0.69.

EXAMPLE IV

3β-Benzoyloxy-6α-chloro-5α-cholest-7ene (7)

To a solution of 1.6M HCl in 100 mL CHCl$_3$ (ethanol-free) at $-65°$ C. is added with stirring a solution of 10.0 g of 3 in 100 mL of CHCl$_3$ (ethanol-free) at $-58°$ C. The resulting amber solution is stirred at $-62°$ C. for 70 seconds and poured into a mixture of 50 mL of concentrated NH$_4$OH and 50 g of ice. The neutralization mixture is swirled vigorously and placed in a separatory funnel. The cold organic layer is drained into 5 mL of pyridine and washed with 2×150 mL of water. After addition of another 5 mL of pyridine, the organic layer is rotary evaporated to a moist solid and dried overnight in vacuo.

A sample of the resulting solid (10.74 g) obtained by the above procedure was analyzed by $^1$H NMR and found to contain 50% 7, 25%, 4a, 5% 3, and 20% of a substance believed to be the 5β-$\Delta^{6,8(14)}$ isomer 8b. After dissolving the crude sample (10.74g) in 30 mL of CHCl$_3$, addition of 60 mL of acetone yields a slowly forming precipitate, which is collected after 30 min by suction filtration. This product (3.38 g) is subjected to five additional recrystallizations to give an analytical sample of 7 (0.37 g) melting over a 2°–3° range at 135° (slow heating) or 155° C. (fast heating). Upon melting, gas was evolved and the product decomposed mainly to 8a (analysis of melted material by $^1$H NMR). The structure of 7 was confirmed by various analytical techniques.

EXAMPLE V

Stability of 7 under various conditions

Solutions of 7 were prepared in EtOAc (1% w/v), anhydrous ether (1%), benzene (1%), and acetone (0.5%). Aliquots of the solutions were removed after 0.5 hours, 24 hours, and 12 days, evaporated to dryness in a stream of nitrogen, dissolved in CDCl$_3$, and immediately analyzed by $^1$H NMR. Any $\Delta^{5,7}$ and $\Delta^{6,8(14)}$ impurities (3, 8a, 8b) could be detected at the 5% level, and $\Delta^{7,14}$ and $\Delta^{8,14}$ impurities (4a, 4b, 9a, 9b) could be detected at the 2% level. No impurities were detected after 0.5 hours or 24 hours in any of the solvents. After 12 days, no decomposition was observed for the EtOAc or benzene solutions. However, 7 had decomposed completely to 8a in ether solution and partially to a mixture including 8a and 3 in the acetone solution.

In other experiments, a 0.13% solution of 7 in cyclohexane stored at 20° C. for 6 weeks showed no decomposition to 8a or any other sterol (2% detection limit). A 0.06% solution of 7 in hexane (Burdick and Jackson)

stored at 20° C. for 30 hours showed decomposition to 8a (admixed with 5-10% each of 11 and 7). Solutions of 50 mg of 7 in 6 mL of CHCl$_3$/methanol (1:1) or CHCl$_3$/ethanol (1:1) each containing 0.1 mL pyridine decomposed completely after 1 hour at 20° C. to a mixture of 3, 8a, and 11.

A 20% solution of 7 decomposed rapidly in CDCl$_3$ solution (contained 5% 8a after 1 hour, decomposed completely to 9a and unidentified sterols after 5 hours) whereas a dilute (2%) solution in CDCl$_3$ decomposed more slowly (approximately 10% each of 8a and 11 after 11 hours). At −20° C., a 2% solution of 7 in CDCl$_3$ was stable for a month. In CHCl$_3$ solution in the absence of base, 7 decomposed to 9a and lesser amounts of unidentified substances. A stirred solution of 7 in CHCl$_3$ containing solid Na$_2$CO$_3$ or pyridine was found after 48 hours to consist primarily of 11 and less than 20% each of 8a and 3. A 2% solution of 7 in CDCl$_3$ containing 10% pyridine or triethylamine showed no detectable decomposition products (<10%) after 3 hours at 20° C. Stirring a solution of 7 in tetrahydrofuran containing solid AgNO$_3$ resulted in a mixture of 3, 8a, and 11. Heating 7 at 80°-120° C. for 10 minutes in an unsealed tube did not lead to detectable (more than 10%) decomposition ($^1$H NMR analysis).

EXAMPLE VI

3β-Benzoyloxy-14 α,15α-epoxy-5α-cholest-7-ene (5).

A solution of 140 g (0.29 mol, 90% pure) of 4a in 5.3 liters of diethyl ether is prepared by gentle warming on a steam bath. This solution is placed in an ice bath and cooled to 24° C., at which time a mixture of 118 g (0.69 mol, 80-85% pure, Aldrich) of MCPBA, 60 g (0.60 mol) of NaHCO$_3$, and 400 mL of diethyl ether is added with vigorous stirring during a 3 minute period in 100 mL portions. The resulting mixture remains in the ice bath at 5° C. for 1 hour while crystallization proceeds. The needle-like crystals of 5 and solid NaHCO$_3$ are collected together by suction filtration and the filter cake dissolved in 1 liter of hot THF. The solution is decanted carefully from the NaHCO$_3$, 2 liters of hexane are added, and the solution allowed to crystallize overnight at −15° C. Filtration affords 105.0 g of colorless crystals (81% yield). The structure of 5 was confirmed by various analytical techniques (mp, IR, and NMR).

Analogous to the above reaction, but on a 1.0 g scale (2.0 mmol) and using 50 mL of solvent (except 100 mL of diethyl ether), reactions were carried out in the following solvents with the isolated yields in parentheses: dibutyl ether (88%), tert-butyl ethyl ether (83%), diisopropyl ether (86%), tert-butyl methyl ether (80%), diethyl ether (76%), CH$_2$Cl$_2$ (77%), and CHCl$_3$ (75%).

A similar reaction using 100 mL of diethyl ether and 25 mL of 0.5M NaHCO$_3$ gave a 75% yield. Use of 99% pure MCPBA instead of 80-85% pure MCPBA did not affect the yield of 5. A series of reactions using 1.0 g of 4a, 40 mL of tert-butyl methyl ether, 0.8 g of MCPBA, and 0.37 g of NaHCO$_3$ was carried out by adding the MCPBA solution when the diene solution had cooled to 28°, 24° and 20° C.; yields 83%, 80%, and 80% were obtained.

EXAMPLE VII

3β-Hydroxy-5α-cholest-8(14)-ene-15-one (1)

A mixture of 120 g (0.238 mol) of 5, 3.0 liters of 95% ethanol, and 350 mL of water in a 5 liter round bottom flask is cooled to 5° C. in an ice bath for 30 minutes. Concentrated H$_2$SO$_4$ (650 mL) is added to this mixture over a period of 10 minutes in 50 mL portions. Any large chunks of suspended material are broken up mechanically. The mixture is heated under reflux for 20-24 hours. The brownish reaction mixture is cooled to 20° C. using an ice bath and then poured into 7 Kg of ice in a 12 liter carboy. The paste-like precipitate is collected on a Büchner funnel using either polypropylene filter cloth (Aldrich) or three layers of Whatman #1 filter paper, which is occasionally scratched to facilitate filtration. The pale-yellow cake is washed three times with 1 liter of cold water and dissolved in 1 liter of hot methanol, to which 1 liter of hexane and 50 mL of hot water are added. The resulting two-phase system is heated on a steam bath until all solid material is dissolved. This mixture is allowed to cool for 2-3 hours to 20° C.; at this point crystals begin to form at the solvent interface. The mixture is then cooled overnight at −15° C. to give a brown upper hexane phase, a lower light yellow aqueous phase, and white crystalline material. The crystals (roughly 90% pure by TLC) are collected by suction filtration and recrystallized again from methanol/hexane/water (2:2:1) as described above.

The resulting material (greater than 95% pure by TLC) is passed through silica gel (200 g, 60-200 mesh, Baker), in a 3 liter glass Büchner funnel with a medium porosity glass fit by eluting with CHCl$_3$. The CHCl$_3$ solution is rotary evaporated to dryness, and the residue is recrystallized from methanol/water to give 66.6 g (70%) of colorless needles.

The structure of a product produced by such a process was confirmed as 1 by known analytical techniques. Samples of 1 stored under nitrogen at 25°, 4°, and −17° C. showed no decomposition (analysis by TLC and HPLC) after two years.

Samples of 1 (in both air and argon), 6, (in argon), and 5 (in both air and argon) were subjected to the above hydrolysis conditions on a small scale. TLC analyses of the crude reaction mixtures showed major spots at R$_f$ 0.70, 0.65 (same R$_f$ as 6), and 0.31. In the case of 5 (but not 1 and 6), and additional major spot at R$_f$ 0.36 (same R$_f$ as 12) was observed. GC and HPLC analyses gave analogous results.

It will be apparent to those with ordinary skill in the art that various modifications to the present invention could be recognized without departing from the scope or spirit of the invention.

What we claim is:

1. A process for converting 3β-benzoyloxycholesta-5,7-diene to 3β-benzoyloxy-5-cholesta-7,14-diene comprising:
    (i) forming a first reaction mixture by contacting 3β-benzoyloxycholesta-5,7-diene, in a solvent at a temperature of at most about −55° C., with HCl at a concentration is said solvent of at least about 2.0M for a time sufficient to convert said 3β-benzoyloxycholesta-5,7-diene to said 3β-benzoyloxy-5-cholesta-7,14-diene;
    (ii) neutralizing the resultant reaction mixture with a base to prevent formation of a significant amount of 3β-benzoyloxy-5-cholesta-8,14-diene; and
    (iii) recovering said 3β-benzoyloxy-5-cholesta-7,14-diene.

2. The process according to claim 1, wherein said 3β-benzoyloxy-5-cholesta-7,14-diene is 3β-benzoyloxy-5α-cholesta-7,14-diene.

3. The process according to claim 1, wherein said 3β-benzoyloxy-5-cholesta-7,14-diene is 3β-benzoyloxy-5β-cholesta-7,14-diene.

4. The process according to claim 1, wherein said HCl concentration is from 2.0M to 2.5M.

5. The process according to claim 4, wherein said temperature is from −65° to −75° C.

6. The process according to claim 1, wherein said HCl is introduced as a gas into said reaction mixture to a concentration of from 2.0 to 2.5M.

7. The process according to claim 1, wherein said solvent comprises a mixture of $CHCl_3$ and $CH_2Cl_2$.

8. The process according to claim 7, wherein said solvent mixture consists of $CHCl_3$ and $CH_2Cl_2$ in approximately a 3:1 ratio.

9. The process according to claim 1, further comprising the step of removing HCl from said reaction mixture through a sodium hydroxide trap prior to said neutralizing.

10. The process according to claim 1, wherein said base is concentrated $NH_4OH$.

11. A process according to claim 1, wherein said 3β-benzoyloxy-5-cholesta-7,14-diene is converted to 3β-benzoyloxy-14α, 15α-epoxy-5-cholest-7-ene a process comprising
   (i) forming a solution of 3β-benzoyloxy-5-cholesta-7,14-diene and ether by heating a mixture thereof and subsequently cooling said solution;
   (ii) forming a second reaction mixture by adding to said solution a mixture comprising an amount of MCPBA and $NaHCO_3$ effective to form and to inhibit the decomposition of said 3β-benzoyloxy-14α, 15α-epoxy-5-cholest-7-ene; and
   (iii) cooling said second reaction mixture to collect said 3β-benzoyloxy-14α, 15α-epoxy-5-cholest-7-ene.

12. The process according to claim 11, wherein said 3β-benzoyloxy-5-cholesta-7,14-diene is 3β-benzoyloxy-5α-cholesta-7,14-diene.

13. The process according to claim 11, wherein said 3β-benzoyloxy-14α,15α-epoxy-5-cholest-7-ene is 3β-benzoyloxy-14α,15α-epoxy-5α-cholest-7-ene.

14. The process according to claim 11, wherein said 3β-benzoyloxy-14α,15α-epoxy-5-cholest-7-ene is 3β-benzoyloxy-14α,15α-epoxy-5β-cholest-7-ene.

15. The process according to claim 11, wherein said 3β-benzoyloxy-5-cholesta-7,14-diene is 3β-benzoyloxy-5-β-cholesta-7,14-diene.

16. The process according to claim 11, wherein said second reaction mixture further comprises said diethyl ether.

17. The process according to claim 11, wherein said second reaction mixture is cooled to about 5° C. for approximately 1 hour to form crystals of said 3β-benzoyloxy-14α,15α-epoxy-5-cholest-7-ene.

18. The process according to claim 11, wherein the ether used in the solution is selected from the group consisting of dibutyl ether, tert-butyl ether, diisopropyl ether, tert-butyl methyl ether, and diethyl ether.

19. The process according to claim 11, wherein the solution of step (i) is a solution of 3β-benzoyloxy-5-cholesta-7,14 diene and a solvent selected from the group consisting of dichloromethane and chloroform.

20. The process according to claim 11, wherein said solution is cooled to about ambient temperature.

21. The process according to claim 1, wherein prior to obtaining said 3β-benzoyloxy-5-cholesta-7,14-diene, said 3β-benzoyloxy-cholesta-5,7-diene is converted to 3β-benzoyloxy-6α-chloro-5α-cholest-7-ene.

22. The process according to claim 1, further comprising the step of monitoring said first reaction mixture to determine when to neutralize said reaction mixture.

23. The process according to claim 22, wherein said monitoring is accomplished by chromatography.

24. The process of claim 1, wherein said 3β-benzoyloxycholesta-5,7-diene is obtained by reacting 7-dehydrocholesterol with benzoyl chloride.

25. The process of claim 24, wherein said 3β-benzoyloxy-5-cholesta-7,14-diene is converted to 3β-benzoyloxy-14α, 15αepoxy-5-cholest-7-ene a process comprising:
   (i) forming a solution of 3β-benzoyloxy-5-cholesta-7,14-diene and diethyl ether by heating a mixture thereof and subsequently cooling said solution;
   (ii) forming a second reaction mixture by adding a mixture comprising MCPBA and $NaHCO_3$ to said solution, and cooling said second reaction mixture to form said 3β-benzoyloxy-14α, 15α-epoxy-5-cholest-7-ene; and
   (iii) collecting said 3β-benzoyloxy-14α, 15α-epoxy-5-cholest-7-ene.

26. The process of claim 25, wherein said 3β-benzoyloxy-14α, 15α-epoxy-5-cholest-7-ene is converted to 5-cholest-8(14)-en-3βol-15 one by reacting said 3β-benzoyloxy-14α, 15α-epoxy-5-cholest-7-ene with a mineral acid in an organic solvent.

27. An intermediate useful in the production of 3β-benzoyloxy-14α, 15α-epoxy-5α-cholest-7-ene, comprising 3β-benzoyloxy-6α-chloro-5α-cholest-7-ene.

28. A process for converting 3β-benzoyloxy-cholesta-5,7-diene to 3β-hydroxy-5-cholest-8(14)-en-15-one comprising the steps:
   (i) forming a first reaction mixture by contacting 3β-benzoyloxy-cholesta-5,7-diene, in a solvent, with HCl at a temperature of at most about −55° C. and a concentration in said solvent of at least about 2.0M for a time sufficient to convert said 3β-benzoyloxy-cholesta-5,7-diene to said 3β-benzoyloxy-5-cholesta-7,14-diene;
   (ii) neutralizing said reaction mixture with a base to prevent formation of a significant amount of 3β-benzoyloxy-5-cholesta-8,14-diene;
   (iii) forming a solution of 3β-benzoyloxy-5-cholesta-7,14-diene and ether and subsequently cooling said solution;
   (IV) forming a second reaction mixture by adding to said solution a mixture comprising an amount of MCPBA and $NaHCO_3$ effective to form and to inhibit the decomposition of said 3β-benzoyloxy-14α, 15α-epoxy-5-cholest-7-ene, cooling said second reaction mixture to collect said 3β-benzoyloxy14α-15α-epoxy-5-cholest-7-ene and
   (v) converting said 3β-benzoyloxy-14α,15 α-epoxy-5-cholest-7-ene to said 3β-hydroxy-5-cholest-8(14)-en-15-one.

29. The process according to claim 28, wherein said 3β-benzoyloxy-5-cholesta-7,14-diene is 3β-benzoyloxy-5α-cholesta-7,14-diene.

30. The process according to claim 28, wherein said 3β-benzoyloxy-5-cholesta-7,14-diene is 3β-benzoyloxy-5β-cholesta-7,14-diene.

31. The process according to claim 28, wherein said HCl concentration is from 2.0M to 2.5M.

32. The process according to claim 31, wherein said temperature is from −65° to −75° C.

33. The process according to claim 28, wherein said HCl is introduced as a gas into said reaction mixture to a concentration of from 2.0 to 2.5M.

34. The process according to claim 28, wherein said solvent comprises a mixture of $CHCl_3$ and $CH_2Cl_2$.

35. The process according to claim 34, wherein said solvent mixture consists of $CHCl_3$ and $CH_2Cl_2$ in approximately a 3:1 ratio.

36. The process according to claim 28, further comprising the step of removing HCl from said reaction mixture through a sodium hydroxide trap prior to said neutralizing.

37. The process according to claim 28, wherein said base is concentrated $NH_4OH$.

38. The process according to claim 28, wherein said 3β-benzoyloxy-14α, 15α-epoxy-5-cholest-7-ene is 3β-benzoylox-14α,15α-epoxy-5α-cholest-7-ene.

39. The process according to claim 28, wherein said 3β-benzoyloxy-14α, 15α-epoxy-5-cholest-7-ene is 3β-benzoyloxy-14α, 15α-epoxy-5β-cholest-7-ene.

40. The process according to claim 28, wherein said second reaction mixture further comprises said ether.

41. The process according to claim 28, wherein prior to obtaining said 3β-benzoyloxy-5-cholesta-7,14-diene in step (i), said 3β-benzoyloxy-cholesta-5,7-diene is converted to 3β-benzoyloxy-6α-chloro-5α-cholest-7-ene.

42. The process according to claim 28, further comprising the step of monitoring said reaction mixture to determine when to neutralize said reaction mixture.

43. The process according to claim 42, wherein said monitoring is accomplished by chromatography.

44. The process according to claim 28, wherein the ether used in the solution is selected from the group consisting of dibutyl ether, tert-butyl ether diisopropyl ether, tert-butyl methyl ether, and diethyl ether.

45. The process according to claim 28, wherein the solution of step (iii) is a solution of 3β-benzoyloxy-5-colesta-7,14 diene and a solvent selected from the group consisting of dichloromethane and chloroform.

46. The process according to claim 28, wherein said solution is cooled to about ambient temperature.

47. The process according to claim 28, further comprising the separation of said 3β-hydroxy-5-cholest-8(14)-en-15-one by using a two-phase recrystallization procedure which comprises
 (i) forming a second solution of alcohol, water and a saturated hydrocarbon with the mixture resulting from said converting step,
 (ii) heating said second solution to form a two-phase system, wherein the first phase contains said saturated hydrocarbon and the second phase contains an alcohol/water mixture,
 (iii) cooling said second solution to to promote the formation of crystals at an interface between said first and second phases which crystals contain said 3β-hydroxy-5-cholest-8(14)-one substantially free of impurities, and
 (iv) collecting said 3β-hydroxy-5-cholest-8(14)-en-15-one.

48. The process according to claim 47, wherein said saturated hydrocarbon is hexane.

49. The process according to claim 47, wherein said alcohol is methanol.

* * * * *